United States Patent [19]

Maurer et al.

[11] 4,152,427
[45] May 1, 1979

[54] COMBATING PESTS WITH SUBSTITUTED PYRIMIDINONE [(DI)-THIO]-PHOSPHORIC(PHOSPHONIC) ACID ESTERS AND ESTER-AMIDES

[75] Inventors: Fritz Maurer, Wuppertal; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 867,259

[22] Filed: Jan. 5, 1978

[30] Foreign Application Priority Data

Jan. 29, 1977 [DE] Fed. Rep. of Germany ....... 2703712

[51] Int. Cl.² .......................... A01N 9/36; C07F 9/65
[52] U.S. Cl. .................................... 424/200; 544/91; 544/244; 544/279; 544/281
[58] Field of Search .................... 260/251 P, 256.4 E, 260/256.5 R; 544/91, 244; 424/200

[56] References Cited

U.S. PATENT DOCUMENTS 3,857,838  12/1974  Perronnet et al. ................ 260/243 R
3,904,624   9/1975  Perronnet et al. ................ 260/251 P Primary Examiner—Donald G. Daus
Assistant Examiner—Diana G. Rivers
Attorney, Agent, or Firm—Sprung, Felfe, Horn, Lynch & Kramer

[57] ABSTRACT

Substituted pyrimidinone [(di)-thio]-phosphoric(phosphonic) acid esters and ester-amides of the formula

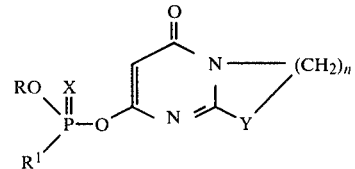

in which
R represents alkyl,
$R^1$ represents alkyl, phenyl, alkoxy, alkylthio or alkylamino,
X represents oxygen or sulphur,
Y represents oxygen or alkylamino, and
n represents 2, 3, or 4, which possess arthropodicidal and nematicidal properties.

10 Claims, No Drawings

COMBATING PESTS WITH SUBSTITUTED PYRIMIDINONE [(DI)-THIO]-PHOSPHORIC(PHOSPHONIC) ACID ESTERS AND ESTER-AMIDES

The present invention relates to and has for its objects the provision of particular new substituted pyrimidinone [(di)-thio]phosphoric(phosphonic) acid esters and ester-amides which possess arthropodicidal and nematicidal properties, active compositions in the form of mixtures of such compounds with solid and liquid dispersible carrier vehicles, and methods for producing such compounds and for using such compounds in a new way especially for combating pests, e.g. anthropods and nematodes, with other and further objects becoming apparent from a study of the within specification and accompanying examples.

It has already been disclosed that O,O-dialkyl-O-pyrimidinyl-thionophosphoric acid esters, for example, O,O-diethyl-O-(2,3-dihydro-5H-thiazolo-[3,2-a]-pyrimidin-5on(7)-yl)- and O,O-diethyl-O-(6,7,8,9-tetrahydro-4H-pyrido[1,2-a]-pyrimidin-4-on-(2)-yl)-thionophosphoric acid esters, possess insecticidal and acaricidal properties (see U.S. Pat. No. 3,857,838 and French Pat. No. 2,197,513).

The present invention now provides, as new compounds, the substituted pyrimidinone [(di)-thio]-phosphoric(phosphonic) acid esters and ester-amides of the general formula

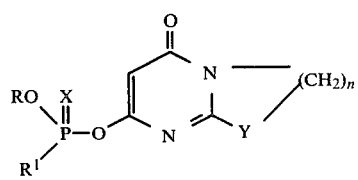

in which
R represents alkyl,
$R^1$ represents alkyl, phenyl, alkoxy, alkylthio or alkylamino,
X represents oxygen or sulphur,
Y represents oxygen or alkylamino and
n represents 2, 3 or 4.

Preferably, R represents straight-chain or branched alkyl with 1 to 6 (especially 1 to 4) carbon atoms, $R^1$ represents phenyl, straight-chain or branched alkyl or alkoxy with 1 to 4 (especially 1 to 3) carbon atoms, or straight-chain or branched alkylthio or monoalkylamino with 1 to 6 (especially 1 to 4) carbon atoms, X represents sulphur, Y represents oxygen or straight-chain or branched alkylamino with 1 to 4 (especially 1 to 3) carbon atoms in the alkyl radical and n represents 2 or 3.

Surprisingly, the substituted pyrimidinone[(di)-thio]-phosphoric(phosphonic) acid esters and ester-amides according to the invention exhibit a substantially better insecticidal, acaricidal and nematicidal action than the corresponding, O,O-dialkyl-O-pyrimidinyl-thionophosphoric acid esters of analogous structure and of the same type of action. The products according to the present invention thus represent a genuine enrichment of the art.

The present invention also provides a process for the preparation of a substituted pyrimidinone[(di)-thio]-phosphoric(phosphonic) acid ester or ester-amide of the formula (I), in which a (thiono)-(thiol)phosphoric(phosphonic) acid ester halide or ester-amide halide of the general formula

in which
R, $R^1$ and X have the above-mentioned meanings and Hal represents halogen, preferably chlorine, is reacted, optionally in the presence of a diluent or solvent, with a hydroxypyrimidinone derivative of the general formula

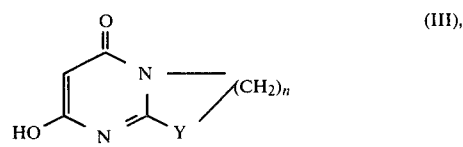

in which
Y and n have the above-mentioned meanings, the latter being employed either in the form of an alkali metal salt, alkaline earth metal salt or ammonium salt or as such in the presence of an acid acceptor.

If, for example, O-sec.-butyl-S-n-propylthionothiolphosphoric acid diester chloride and 1,2,3,4-tetrahydro-1-methyl-6H-8-hydroxy-pyrimido[1,2-a]-pyrimidin-6-one are used as starting compounds, the course of the reaction can be represented by the following equation:

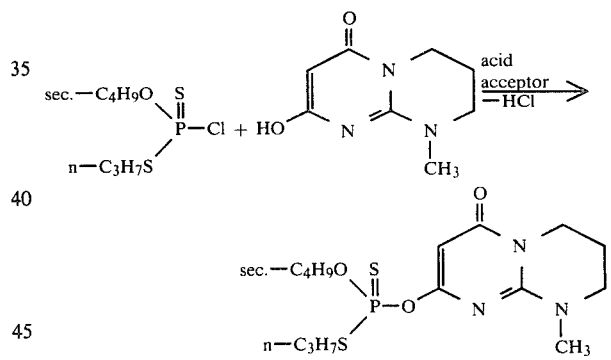

The (thiono)(thiol)phosphoric(phosphonic) acid ester halides and ester-amide halides (II) to be used as starting materials are described in the literature and can be prepared in accordance with known processes.

The following may be mentioned individually as examples: O,O-dimethyl-, O,O-diethyl-, O,O-di-n-propyl-, O,O-di-isopropyl-, O,O-di-n-butyl-, O,O-di-iso-butyl-, O,O-di-sec.-butyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-iso-propyl-, O-ethyl-O-n-butyl-, O-ethyl-O-sec.-butyl-, O-ethyl-O-iso-butyl-, O-n-propyl-O-butyl- and O-iso-propyl-O-butylphosphoric acid diester chloride and the corresponding thiono analogues; O,S-dimethyl-, O,S-diethyl-, O,S-di-n-propyl-, O,S-di-iso-propyl-, O,S-di-n-butyl-, O,S-di-iso-butyl-, O-ethyl-S-n-propyl-, O-ethyl-S-iso-propyl-, O-ethyl-S-n-butyl-, O-ethyl-S-sec.butyl-, O-n-propyl-S-ethyl-, O-n-propyl-S-iso-propyl-, O-n-butyl-S-n-propyl- and O-sec.-butyl-S-ethylthiolphosphoric acid diester chloride and the corresponding thiono analogues; O-methyl-, O-ethyl-, O-n-propyl-, O-iso-propyl-, O-n-butyl-, O-iso-butyl- and O-sec.-butyl-methane-, -ethane-, -n-propane-, -iso-propane-, -n-butane, -iso-butane-, -tert.-butane-, -sec.-butane- and -phenyl-phosphonic acid ester chloride and the corresponding thiono analogues; and O-methyl-N-methyl-, O-methyl-N-ethyl-, O-methyl-N-n-propyl-, O-methyl-N-iso-propyl-, O-ethyl-N-methyl-, O-ethyl-N-ethyl, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-iso-propyl-, O-isopropyl-N-methyl-, O-iso-propyl-N-ethyl-, O-iso-propyl-N-n-propyl, O-iso-propyl-N-iso-propyl-, O-n-butyl-N-methyl-, O-n-butyl-N-ethyl-, O-n-butyl-N-n-propyl-, O-n-butyl-N-iso-propyl-, O-iso-butyl-N-methyl-, O-iso-butyl-N-ethyl-, O-iso-butyl-N-n-propyl-, O-iso-butyl-N-iso-propyl-, O-sec.butyl-N-methyl-, O-sec.-butyl-N-ethyl-, O-sec.-butyl-N-n-propyl- and O-sec.-butyl-N-iso-propyl-phosphoric acid monoester-amide chloride and the corresponding thiono analogues.

The hydroxypyrimidinone derivatives (III) to be used as starting material have not been described in the literature, but can be prepared in accordance with known processes, by reacting malonic acid dialkyl esters with 1-alkyl-2-amino-tetrahydro-pyrimidine hydrohalide in the presence of an alcoholate or reacting an ω-halogenoalkyl-amine hydrohalide, in a first reaction, with an alkali metal cyanate, and reacting the reaction product, in a second reaction, with an alcoholate and then with a dialkyl malonate.

The following may be mentioned as individual examples of the above derivatives (III): 2,3-dihydro-5H-7-hydroxyoxazolo-[3,2-a]-pyrimidin-5-one, 2,3,4-trihydro-6H-8-hydroxypyrimido-[2,1-b]-1,3-oxazin-6-one, 1,2,3,4-tetrahydro-1-methyl-6H-8-hydroxy-pyrimido[1,2-a]-pyrimidin-6-one, 1,2,3,4-tetrahydro-1-isopropyl-6H-8-hydroxy-pyrimido[1,2-a]pyrimidin-6-one, 1,2,3-trihydro-1-methyl-5H-7-hydroxy-imidazo[1,2-a]-pyrimidin-5-one and 1,2,3-trihydro-1-isopropyl-5H-7-hydroxy-imidazo[1,2-a]-pyrimidin-5-one.

The process for the preparation of the compounds according to the invention is preferably carried out in the presence of a suitable solvent or diluent. Virtually all inert organic solvents can be used for this purpose, especially aliphatic and aromatic, optionally chlorinated, hydrocarbons, for example benzene, toluene, xylene, benzine, methylene chloride, chloroform, carbon tetrachloride and chlorobenzene; ethers, for example diethyl ether, bibutyl ether and dioxane; ketones, for example acetone, methyl ethyl ketone, methyl isopropyl ketone and methyl isobutyl ketone; and nitriles, such as acetonitrile and propionitrile.

All conventional acid-binding agents can be used as acid acceptors. Alkali metal carbonates and alkali metal alcoholates, such as sodium carbonate and potassium carbonate, sodium methylate and ethylate and potassium methylate, ethylate and tert.-butylate, have proved particularly suitable, as have aliphatic, aromatic or heterocyclic amines, for example triethylamine, trimethylamine, dimethylaniline, dimethylbenzylamine and pyridine.

The reaction temperature can be varied within a substantial range. In general, the reaction is carried out at from 0° to 140° C., preferably at from 30° to 80° C.

In general, the reaction is allowed to take place under normal pressure.

To carry out the process, the starting components are in most cases employed in stoichiometric amounts. An excess of one or the other reactant produces no significant advantages. The reactants are, in general, brought together in one of the above solvents and are stirred for several hours, in most cases at an elevated temperature, to complete the reaction. Thereafter, an organic solvent, for example toluene, is added and the organic phase is worked up in the usual manner by washing, drying and distilling off the solvent.

The new compounds are frequently obtained in the form of oils, some of which cannot be distilled without decomposition but are freed from the last volatile constituents by so-called "slight distillation", that is to say by prolonged heating under reduced pressure to moderately elevated temperatures, and are purified in this manner. They are characterized by the refractive index. Some compounds are obtained in a crystalline form and are characterized by their melting point.

As already mentioned, the compounds according to the present invention are distinguished by an excellent insecticidal, acaricidal and nematicidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant production and in the hygiene field and the field of protection of stored products.

The active compounds are well tolerated by plants, have a favorable level of toxicity to warm-blooded animals, and can be used for combating arthropod pests, especially insects and acarids, and nematodes which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana,* Leucophaea maderae, *Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaste spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia keuhniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example Scorpio maurus and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, wettable powders. suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g., acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthorpodicides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contemplates methods of selectively killing, combating or controlling pests, e.g. arthropods and nematodes, which comprises applying to at least one of correspondingly (a) such arthropods, (b) such nematodes, and (c) the corresponding habitat thereof, i.e. the locus to be protected, e.g. to a growing crop, to an area where a crop is to be grown or to a domestic animal, a correspondingly combative or toxic amount, i.e. an arthropodicidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

The pyrimidinones (III) to be used as starting materials could be prepared, for example, as follows:

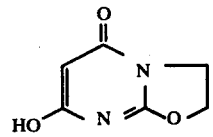

a:

A mixture of 34.8 g (0.3 mol) of β-chloroethylamine hydrochloride, 24.3 g (0.3 mol) of potassium cyanate and 60 ml of water was boiled for 1.5 hours under reflux. 100 ml of ethanol were then added, the mixture was filtered and the residue was rinsed with ethanol. The filtrate was evaporated to dryness in vacuo and the residue was dissolved in 200 ml of methanol. A solution of 32.4 g (0.6 mol) of sodium methylate in 150 ml of methanol was then added, 48 g (0.3 mol) of diethyl malonate were then introduced into the reaction mixture and the batch was boiled for 24 hours under reflux. The solvent was distilled off in vacuo and the residue was dissolved in 150 ml of warm water. Concentrated hydrochloric acid was then added, while stirring, until a pH value of about 4 was reached. The solution was cooled for 1 hour in an ice-bath and the product which had precipitated was then filtered off and rinsed with a little ice-water. 21.2 g (46% of theory) of 2,3-dihydro-5H-7-hydroxy-oxazolo[3,2-a]-pyrimidin-5-one were thus obtained in the form of colorless crystals of melting point 222° C.

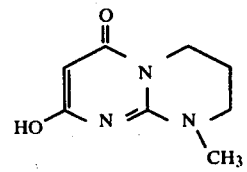

b:

A mixture of 130 g (0.67 mol) of 1-methyl-2-amino-1,4,5,6-tetrahydropyrimidine hydrobromide, 73 g (1.35 mol) of sodium methylate, 520 ml of methanol and 107.2 g (0.67 mol) of diethyl malonate was boiled for 4 hours under reflux. The solvent was then distilled off in vacuo and the residue was dissolved in 300 ml of water. The solution was brought to pH 4–5 by adding concentrated hydrochloric acid while cooling the solution in an ice-bath. After 1 hour, the product which had crystallized out was filtered off and rinsed with a little ice-water. 62 g (52% of theory) of 1,2,3,4-tetrahydro-1-methyl-6H-8-hydroxy-pyrimido[1,2-a]-pyrimidin-6-one were thus obtained in the form of colorless crystals of melting point 243° C. (with decomposition).

The following compounds could be prepared analogously:

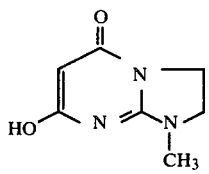

in a yield of 61% of theory, and with a melting point of 221° C. (with decomposition)

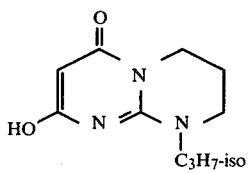

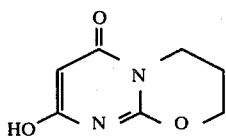

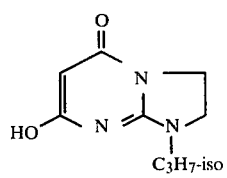

EXAMPLE 2

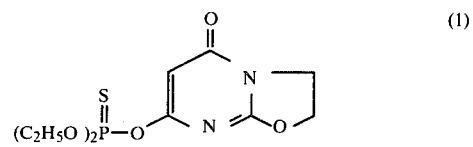  (I)

A mixture of 15.4 g (0.1 mol) of 2,3-dihydro-5H-7-hydroxy-oxazolo-[3,2-a]-pyrimidin-5-one, 16.6 g (0.12 mol) of potassium carbonate, 200 ml of acetonitrile and 18.9 g (0.1 mol) of O,O-diethylthionophosphoric acid diester chloride was stirred for 17 hours at 45° C. 300 ml of toluene were then added and the reaction mixture was extracted by shaking twice with 300 ml of water each time. The organic phase was dried over sodium sulphate and the solvent was then distilled off in vacuo. The residue was subjected to slight distillation at about 80° C. 18.1 g (59% of theory) of O,O-diethyl-O-(2,3-dihydro-5H-oxazolo-[3,2-a]-pyrimidin-5-on-7-yl)-thionophosphoric acid ester were thus obtained in the form of a brown oil having a refractive index $n_D^{22}$ of 1.5387.

The following compounds of the formula

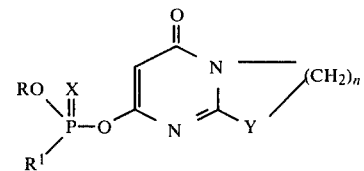  (I)

could be prepared analogously:

TABLE 2

| Compound No. | R | $R^1$ | X | Y | n | Yield (% of theory) | Physical data (refractive index; melting point ° C.) |
|---|---|---|---|---|---|---|---|
| 2 | $C_2H_5$ | $C_2H_5$ | S | O | 2 | 62 | $n_D^{22}$:1.5550 |
| 3 | $CH_3$ | $OCH_3$ | S | O | 2 | 42 | 60 |
| 4 | n-$C_3H_7$ | $OC_2H_5$ | S | O | 2 | 59 | $n_D^{25}$:1.5300 |
| 5 | $C_2H_5$ | $OC_2H_5$ | S | N-$CH_3$ | 3 | 56 | 72 |
| 6 | $CH_3$ | $OCH_3$ | S | N-$CH_3$ | 3 | 38 | 110 |
| 7 | $C_2H_5$ | $C_2H_5$ | S | N-$CH_3$ | 3 | 64 | 78 |
| 8 | $C_2H_5$ | $OC_2H_5$ | S | N-$CH_3$ | 2 | 54 | 76 |
| 9 | $CH_3$ | $OCH_3$ | S | N-$CH_3$ | 2 | 47 | 118 |
| 10 | $C_2H_5$ | $C_2H_5$ | S | N-$CH_3$ | 2 | 57 | 54 |
| 11 | $C_2H_5$ | $C_2H_5$ | O | O | 2 | | |
| 12 | $C_2H_5$ | $SC_3H_7$-n | S | O | 2 | 53 | $n_D^{24}$:1.5689 |
| 13 | iso-$C_3H_7$ | $CH_3$ | S | O | 2 | 69 | 90 |
| 14 | $C_2H_5$ | phenyl | S | O | 2 | 48 | $n_D^{23}$:1.6214 |
| 15 | $C_2H_5$ | NH-$C_3H_7$-iso | S | O | 2 | | |
| 16 | $C_2H_5$ | $OC_2H_5$ | S | O | 3 | | |
| 17 | $CH_3$ | $OCH_3$ | S | O | 3 | | |
| 18 | $C_2H_5$ | $C_2H_5$ | S | O | 3 | | |
| 19 | $C_2H_5$ | $OC_2H_5$ | S | N-$C_3H_7$-iso | 2 | | |
| 20 | $CH_3$ | $OCH_3$ | S | N-$C_3H_7$-iso | 2 | | |
| 21 | $C_2H_5$ | $OC_2H_5$ | S | N-$C_3H_7$-iso | 3 | | |
| 22 | $CH_3$ | $OCH_3$ | S | N-$C_3H_7$-iso | 3 | | |
| 23 | $C_2H_5$ | $OC_2H_5$ | O | O | 2 | 71 | $n_D^{24}$:1.4971 |
| 24 | $C_2H_5$ | $SC_3H_7$-n | O | O | 2 | 50 | $n_D^{23}$:1.5396 |

The insecticidal, acaricidal or nematicidal activity of the compounds of this invention is illustrated by the following examples wherein the compounds according to the present invention are each identified by the number (given in brackets) from the preparative examples hereinabove.

The known comparison compounds are identified as follows:

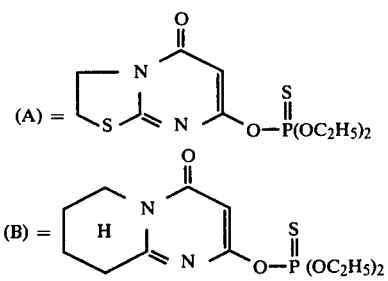

EXAMPLE 3

Drosophila test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier, and the concentrate was diluted with water to the desired concentration.

1 ml of the preparation of the active compound was applied with a pipette to a filter paper disc of 7 cm diameter. The wet disc was placed over the orifice of a glass vessel containing 50 vinegar flies (*Drosophila melanogaster*) and covered with a glass plate.

After the specified periods of time, the destruction was determined in %. 100% meant that all of the flies were killed; 0% meant that none of the flies were killed.

The active compounds, the concentrations of the active compounds, the evaluation times and the results can be seen from the following table:

Table 3

| Active compounds | (insects which damage plants) | |
|---|---|---|
| | Drosophila Test | |
| | Active compound concentration in % | Degree of destruction in % after 1 day |
| (A) | 0.01 | 100 |
| | 0.001 | 0 |
| (B) | 0.01 | 100 |
| | 0.001 | 0 |
| (5) | 0.01 | 100 |
| | 0.001 | 100 |
| (8) | 0.01 | 100 |
| | 0.001 | 100 |
| (14) | 0.01 | 100 |
| | 0.001 | 100 |

EXAMPLE 4

Phaedon larvae test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

Table 4

| Active compounds | (insects which damage plants) | |
|---|---|---|
| | Phaedon larve Test | |
| | Active compound concentration in % | Degree of destruction in % after 3 days |
| (A) | 0.01 | 100 |
| | 0.001 | 0 |
| (B) | 0.01 | 100 |
| | 0.001 | 0 |
| (1) | 0.01 | 100 |
| | 0.001 | 100 |
| (2) | 0.01 | 100 |
| | 0.001 | 90 |
| (4) | 0.01 | 100 |
| | 0.001 | 90 |

EXAMPLE 5

Tetranychus test (resistant)
Solvent: 3 parts by weight of acetone
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 5

| Active compounds | (mites which damage plants) | |
|---|---|---|
| | Tetranychus Test | |
| | Active compound concentration in % | Degree of destruction in % after 2 days |
| (3) | 0.1 | 99 |
| | 0.01 | 70 |
| (1) | 0.1 | 100 |
| | 0.01 | 99 |
| (23) | 0.1 | 99 |
| | 0.01 | 70 |
| (2) | 0.1 | 100 |
| | 0.01 | 99 |
| (13) | 0.1 | 100 |
| | 0.01 | 100 |
| (2) | 0.1 | 100 |
| | 0.01 | 99 |

EXAMPLE 6

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27°.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

The active compound, the amounts applied and the results can be seen from the following table:

Table 6

| Active compound | (nematodes which damage plants) Meloidogyne incognita Degree of destruction in % at an active compound concentration of 5 ppm |
|---|---|
| (B) | 0 |
| (A) | 0 |
| (1) | 100 |
| (4) | 100 |

It will be appreciated that the instant specification and claims are set forth by way of illustration and not limitation, and that various modifications and changes may be made without departing from the spirit and scope of the present invention.

What is claimed is:

1. A compound of the formula

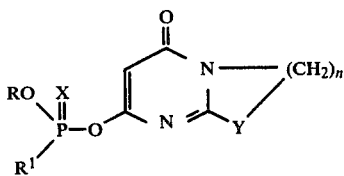

in which
R represents alkyl with 1 to 6 carbon atoms,
R¹ represents alkyl or alkoxy with 1 to 4 carbon atoms, or phenyl, alkylthio or alkylamino with 1 to 6 carbon atoms in each alkyl radical,
X represents oxygen or sulphur,
Y represents oxygen or alkylamino with 1 to 4 carbon atoms in the alkyl radical and
n represents 2, 3 or 4.

2. A compound according to claim 1, in which
X is sulphur,
Y is oxygen, and
n is 2 or 3.

3. A compound according to claim 1, wherein such compound is O,O-diethyl-O-(2,3-dihydro-5H-oxazolo-[3,2-a]-pyrimidin-5-on-7-yl)-thionophosphoric acid ester of the formula

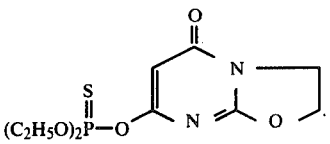

4. A compound according to claim 1, wherein such compound is O-ethyl-O-(2,3-dihydro-5H-oxazolo-[3,2-a]-pyrimidin-5-on-7-yl)-ethanethionophosphonic acid ester of the formula

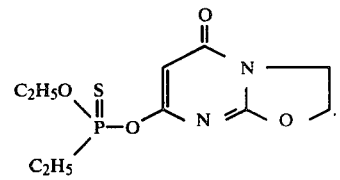

5. A compound according to claim 1, wherein such compound is O,O-dimethyl-O-(2,3-dihydro-5H-oxazolo-[3,2-a]-pyrimidin-5-on-7-yl)-thionophosphoric acid ester of the formula

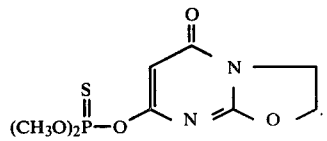

6. A compound according to claim 1, wherein such compound is O,O-diethyl-O-(1,2,3,4-tetrahydro-1-methyl-6H-pyrimido[1,2-a]-pyrimidin-6-on-8-yl)-thionophosphoric acid ester of the formula

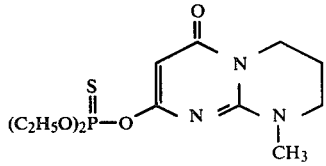

7. A compound according to claim 1, wherein such compound is O-ethyl-O-2,3-dihydro-5H-oxazolo-[3,2-a]-phenylthionophosphonic acid ester of the formula

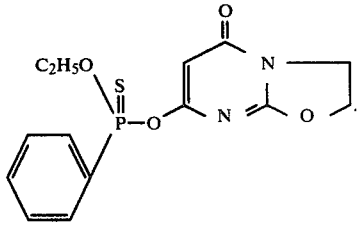

8. An arthropodicidal or nematicidal composition containing as active ingredient an arthropodicidally or nematicidally effective amount of a compound according to claim 1 in admixture with a diluent.

9. A method of combating arthropods or nematodes which comprises applying to the arthropods or nematodes, or to a habitat thereof, an arthropodicidally or nematicidally effective amount of a compound according to claim 1.

10. The method according to claim 9 in which said compound is

O,O-diethyl-O-(2,3-dihydro-5H-oxazolo-[3,2-a]-pyrimidin-5-on-7-yl)-thionophosphoric acid ester,
O-ethyl-O-(2,3-dihydro-5H-oxazolo-[3,2-a]-pyrimidin-5-on-7-yl)-ethanethionophosphonic acid ester.
O,O-dimethyl-O-(2,3-dihydro-5H-oxazolo-[3,2-a]-pyrimidin-5-on-7-yl)-thionophosphoric acid ester,
O,O-diethyl-O-(1,2,3,4-tetrahydro-1-methyl-6H-pyrimido[1,2a]-pyrimidin-6-on-8-yl)-thionophosphoric acid ester, or
O-ethyl-O-(2,3-dihydro-5H-oxazolo-[3,2-a]-pyrimidin-5-on-7-yl)-phenylthionophosphonic acid ester.

* * * * *